(12) United States Patent
Kobayashi et al.

(10) Patent No.: US 6,720,063 B2
(45) Date of Patent: Apr. 13, 2004

(54) ELASTICALLY STRETCHABLE COMPOSITE SHEET AND PROCESS FOR MAKING THE SAME

(75) Inventors: Toshio Kobayashi, Kagawa-ken (JP); Hiroki Goda, Kagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 7 days.

(21) Appl. No.: 09/941,566

(22) Filed: Aug. 30, 2001

(65) Prior Publication Data

US 2002/0061390 A1 May 23, 2002

(30) Foreign Application Priority Data

Jan. 9, 2000 (JP) .................................. 2000-266084

(51) Int. Cl.⁷ .............................................. B32B 27/12
(52) U.S. Cl. ..................... 428/196; 428/198; 428/397; 442/328; 442/337; 442/182; 442/195; 442/239; 442/268; 442/381; 156/166; 156/299
(58) Field of Search ................... 428/196, 198, 428/397; 442/337, 328, 182, 195, 239, 268, 381; 156/166, 299

(56) References Cited

U.S. PATENT DOCUMENTS

| 5,759,926 A | 6/1998 | Pike et al. |
| 5,935,883 A | 8/1999 | Pike |
| 5,939,178 A | * 8/1999 | Boich .......................... 428/198 |

FOREIGN PATENT DOCUMENTS

| DE | 4243012 | * 6/1994 |
| JP | 1996-504693 | 5/1996 |
| WO | WO 96/38620 | 12/1996 |

* cited by examiner

*Primary Examiner*—Elizabeth M. Cole
(74) *Attorney, Agent, or Firm*—Lowe Hauptman Gilman & Berner LLP (57) ABSTRACT

An elastically stretchable composite sheet includes an elastically stretchable first web and an inelastically stretchable second web of thermoplastic synthetic resin fiber which is intermittently bonded to the first web in a y-direction. Component fiber of the second web has its cress-section cut in a direction orthogonal to the y-direction defined by a width w and a height h dimensioned to be at a ratio h/w less than 0.5. The composite sheet having such a structure improve its flexibility.

16 Claims, 5 Drawing Sheets

ELASTICALLY STRETCHABLE COMPOSITE SHEET AND PROCESS FOR MAKING THE SAME

BACKGROUND OF THE INVENTION

This invention relates to an elastically stretchable composite sheet and a process for making the same.

Japanese Patent Application (PCT) Publication No. 1996-504693A describes a multilayered elastic panel and a process for making the same. This elastic layer comprises a rubber elastic layer and an inelastic fibrous layer bonded to the former in bonding zones so that the inelastic fibrous layer forms gathers between each pair of the adjacent bonding zones. The inelastic fibrous layer is formed with fibers obtained with spun bonding process or melt blown process.

While it is possible for the prior art to obtain fine fibers having a fineness less than 0.1 dtex using the melt blown process, it is difficult for the prior art to control a cross-section presented by each of these fibers in a predetermined shape. This process is thus unsuitable for improvement of fiber surface luster by flattening the cross-sectional shape of the fiber. In addition to this, it is impossible for this process to use the nozzles each having a relatively large diameter and therefore it is difficult for this process to increase discharge from each nozzle per unit time and thereby to improve a productivity of the fiber. While such drawback of the melt blown process may be eliminated by use of the spun bonding process, it is difficult for this spun bonding process to obtain fine fibers of a fineness less than 1 dtex at a high efficiency and therefore it is difficult for this process to obtain comfortably flexible fibrous layer offered by the fibers of adequately low fineness.

SUMMARY OF THE INVENTION

It is an object of this invention to eliminate the drawbacks involved in the composite sheet comprising the elastically stretchable layer and the inelastically stretchable fibrous layer and the process for making the same, for example, as disclosed in the Publication.

According to a first aspect of this invention, there is provided an elastically stretchable composite sheet and, according to a second aspect of this invention, there is provided a process for making the composite sheet.

The first aspect of this invention relates to an elastically stretchable composite sheet comprising a first web having x- and y-directions orthogonal to each other and being elastically stretchable at least in the y-direction and a second web made of thermoplastic synthetic resin fibers and being inelastically stretchable in the y-direction, the first and second webs being bonded to each other in bonding zones intermittently arranged in the y-direction wherein a length of the thermoplastic synthetic resin fiber bonded to the first web measured between each pair of the adjacent bonding zones is longer than a straight distance defined between the pair of the adjacent bonding zones.

The improvement according to this invention in the composite sheet is in that the fiber has in its cross-section cut in a direction orthogonal to its longitudinal direction a width w and a height h orthogonal to the width w dimensioned so that a ratio of h/w is less than 0.5.

The second aspect of this invention relates to a process for making an elastically stretchable composite sheet comprising first web having x- and y-directions orthogonal to each other and being elastically stretchable at least in the y-direction and second web made of a plurality of thermoplastic synthetic resin fibers and being inelastically stretchable in the y-direction, the first and second webs being bonded to each other in bonding zones intermittently arranged in the y-direction wherein a length of the thermoplastic synthetic resin fiber bonded to the first web measured between each pair of the adjacent bonding zones is longer than a straight distance defined between the pair of the adjacent bonding zones.

The improvement according to the second aspect of this invention in the process for making the composite sheet comprising the steps of:

a. continuously feeding the first web in the y-direction;

b. obtaining conjugated fibers each comprising at least two types of thermoplastic synthetic resin and being dividable into the at least two types of resin by melt spinning and then continuously feeding an assembly of the conjugated fibers in the form of web in the y-direction for said second web;

c. placing the first web and the web of conjugated fibers for said second web upon each other and bonding these two webs together in bonding zones arranged intermittently in the y-direction to form a composite web;

d. stretching the composite web in the y-direction and obtaining the second web from the web of conjugated fibers; and e. contracting the stretched composite web to obtain the composite sheet.

According to one preferred embodiment of this invention, further comprising a step of continuously feeding the composite web in stretched or contracted state and subjecting the conjugated fibers to high pressure columnar water streams discharged from a plurality of nozzles to divide each of the conjugated fibers.

DETAILED DESCRIPTION OF THE PREFERRED EMBODIMENTS

Details of an elastically stretchable composite sheet and a process for making the same according to this invention will be more fully understood from the description with reference to the accompanying drawings.

Figure 1:
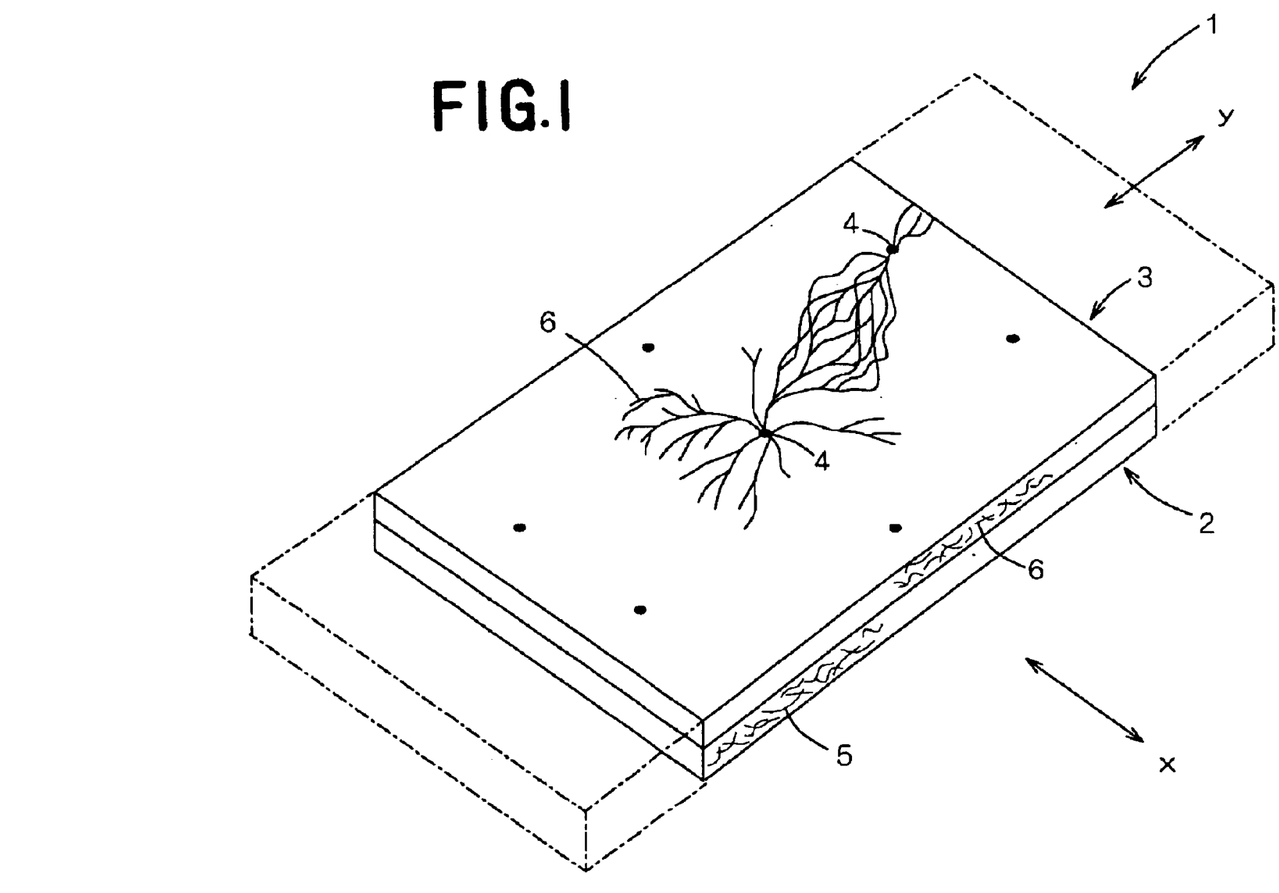
FIG. 1 is a perspective view of a composite sheet according to this invention.

FIG. 1 is a perspective view showing an elastically stretchable composite sheet 1 obtained using a process according to this invention. The composite sheet 1 can be suitably used as liquid-pervious or liquid-impervious topsheet in disposable wearing articles such as a disposable diaper, a sanitary napkin or a disposable gown used in medical field. In the case of the embodiment as shown, the composite sheet 1 has a lower layer 2 and an upper layer 3 integrally welded or bonded together at bonding zones 4. The composite sheet 1 is elastically stretchable at least a y-direction orthogonal to a x-direction, as indicated by chain lines. FIG. 1 shows only a part of component fibers 5, 6 forming the lower layer 2 and upper layer 3.

The lower layer 2 of the composite sheet 1 is elastically stretchable in the y-direction, preferably both in the y- and x-directions. Such layer 2 is formed with a fibrous assembly consisting of short fiber, long fibers or continuous fibers made of elastic material such as thermoplastic elastomer or with film or the like made of such elastic material. In the case of the lower layer 2 formed with the fibers 5 as shown, this lower layer 2 is a preferably a nonwoven or woven fabric in which the fibers are intertwined under mechanical effect or under welding or adhesively bonding effect. The lower layer 2 is elastically stretched as the composite sheet 1 is elastically stretched in the y-direction under an external force exerted thereon and the composite sheet 1 contracts again as it is relieved of the external force.

The upper layer 3 of the composite sheet 1 is inelastically stretchable at least in the y-direction of x- and y-directions. Such upper layer 3 is an assembly of thermoplastic synthetic resin fibers 6 each continuously extending between each pair of the adjacent bonding zones 4, 4. The fibers 6 are short fibers, preferably long fibers and more preferably continuous fibers. A length of the individual fiber's section defined between each pair of the adjacent bonding zones 4, 4 is longer than a straight distance between these adjacent bonding zones 4, 4 and full length of the individual fiber 6 describes an irregular curve over an entire surface of the upper layer 3. The fibers 6 are reoriented between the respective pairs of the adjacent bonding zones 4, 4 to describe straight lines extending in the y-direction as the composite sheet 1 is stretched in the y-direction. These fibers 6 describe again the curves as the composite sheet 1 contacts again. In the illustrated embodiment, the upper layer 3 is welded to the lower layer 2 at the bonding zone 4 and a plurality of the fibers 6 at the bonding zones 4 are welded together in film-like state.

Figure 2:
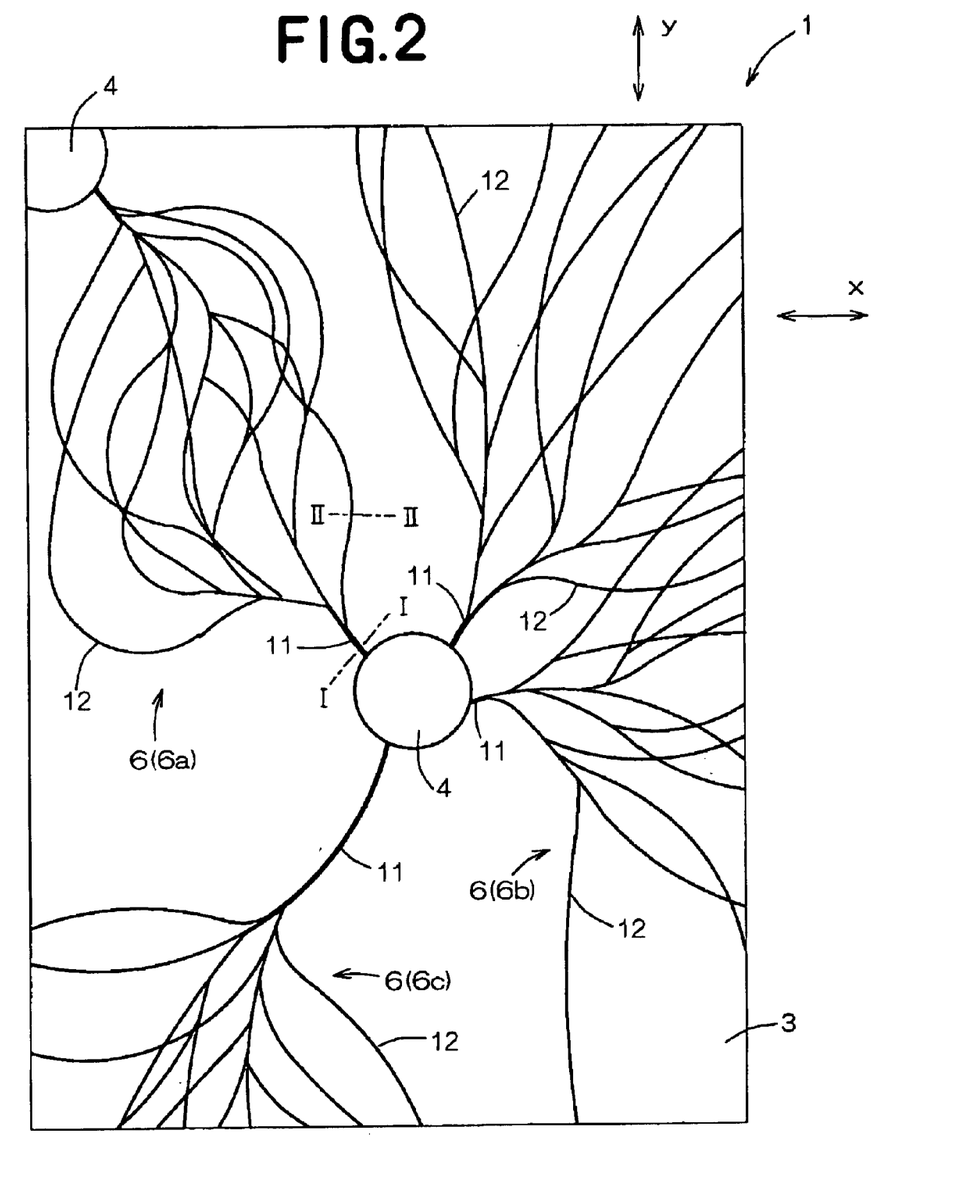
FIG. 2 is a fragmentary plan view showing the composite sheet.

FIG. 2 is a fragmentary plan view showing the composite sheet 1 with the upper layer 3 overlying the lower layer 2. Referring to FIG. 2, one type of fibers 6a in the plural fibers 6 forming the upper layer 3 have high fineness diameter-enlarged portions 11 in the vicinity of the respective bonding zones 4, each of these portions 11 are branched into a plurality of diameter-reduced portions 12 at a slight distance from the bonding zones 4. Another type of fibers 6b in the plural fibers 6 also have the diameter-enlarged portions 11 which are substantially shorter than the diameter-enlarged portion 11 of the one type of fibers 6b and branched into the diameter-reduced portions 12 in the vicinity of the respective bonding zones 4. Still another type of fibers 6c of the plural fibers 6 also have the diameter-enlarged portions 11 which are relatively long and branched into the diameter-reduced portions 12 at relatively large distance from the respective bonding zones 4.

Figure 3A:
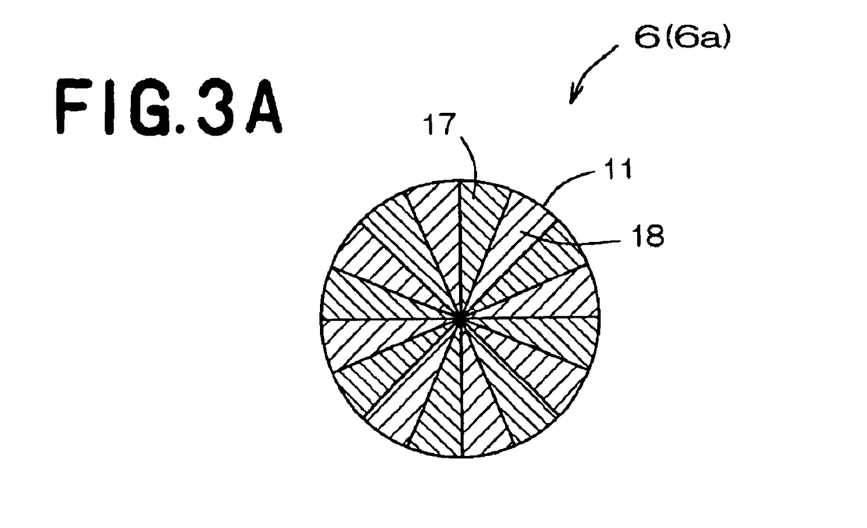
FIG. 3 is sectional views of a component fiber as taken along a diameter-enlarged portion (A) and a diameter-reduced portion (B) thereof.
Figure 3B:
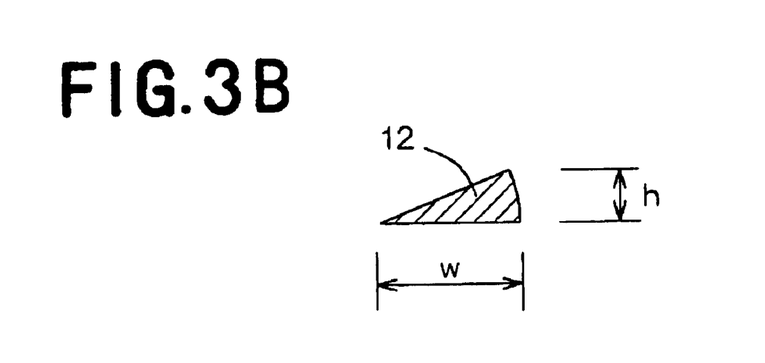
Figure 4A:
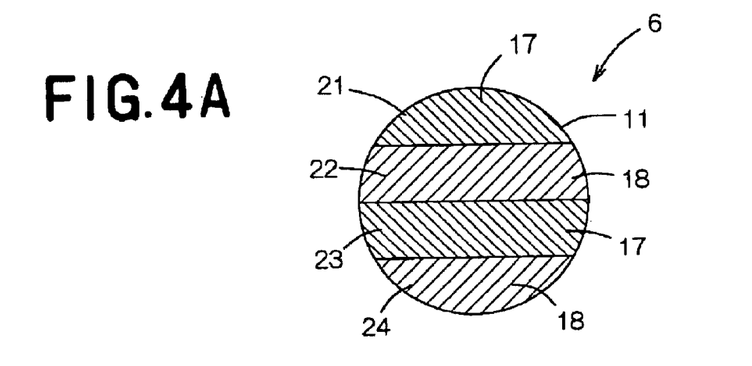
FIG. 4 is sectional views similar to FIG. 3 but of an alternative embodiment of the component fiber.
Figure 4B:
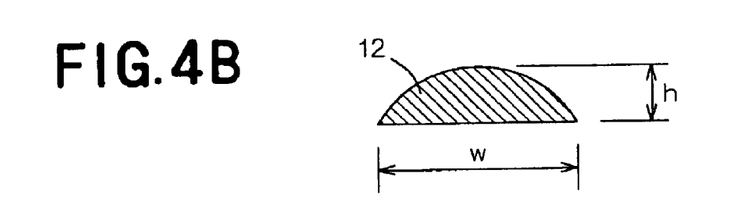
Figure 4C:
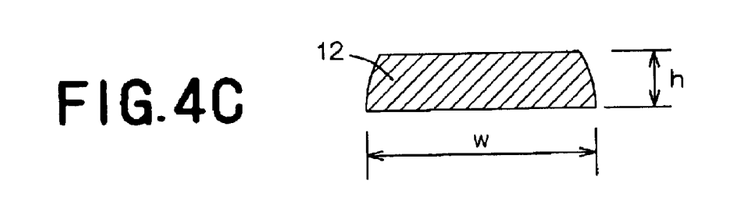
Figure 4D:
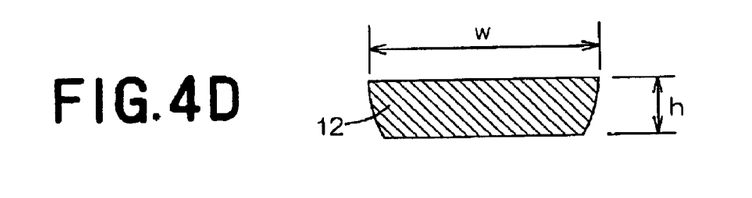
Figure 4E:
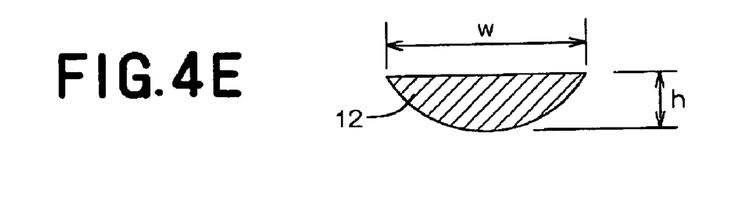

Of FIG. 3, (A) and (B) are sectional views of the fiber 6a taken along a line I—I and a line II—II in FIG. 2, respectively. FIG. 3 (A) schematically illustrates a section of the diameter-enlarged portion 11 of the fiber 6a. The fiber 6a is a conjugated fiber made of polypropylene resin and polyester resin and its diameter-enlarged portion 11 has a fineness, for example, of 8 dtex. Polypropylene resin layers 17 and polyester resin layers 18 alternate so as to divide equally the fiber 6a into 16 sections circumferentially of the fiber 6a. FIG. 3 (B) schematically illustrates a section of one of the diameter-reduced portions 12 generated as the respective resin layers 17, 18 of the diameter-enlarged portion 11 have been branched. The diameter-reduced portion 12 has a width w as measured in horizontal and a height h as measured in the direction orthogonal to the width w. A ratio of the height h to the width w, i.e., h/w is preferably less than 0.5. From the diameter-enlarged portion 11 having the fineness of 8 dtex, the diameter-reduced portion 12 having a fineness of approximately 0.5 dtex is obtained.

Even if the fiber 6 has a relatively large diameter in its diameter-enlarged portions 11, the fiber 6 is branched into the diameter-reduced portions 12 in the vicinity of the respective bonding zones 4 and offers a comfortably soft touch. The diameter-reduced portions 12 each presenting a flat section defined by the ratio h/w less than 0.5 may readily spread on the surface of the sheet 1 with their width w extending in horizontal. Such diameter-reduced portions 12 are easily deformable particularly in a thickness direction of the composite sheet 1 and thereby make the composite sheet 1 flexible. Flatness of the diameter-reduced portion 12 facilitates the fiber 6 to be deformed in the direction of the height h in comparison to ordinary fiber being substantially circular in its cross-section and having the same sectional area as that of the diameter-reduced portion 12. The diameter-reduced portions 12 are able to provide the composite sheet 1 with luster peculiar to the flat fiber.

Of FIG. 4, (A) schematically illustrates a section of the diameter-enlarged portion 11 in the fiber 6 of construction different from the fiber 6 illustrated in FIG. 3. (B)~(E) of FIG. 4 schematically illustrate sections of the diameter-reduced portions 12 respectively branched from the diameter-enlarged portion 11. A circular cross-section of the diameter-enlarged portion 11 is divided equally into four layers comprising the polypropylene resin layers 17 and the polyester resin layers 18 alternately placed one upon another. Four resin layers 17, 18 divided in this manner respectively define the diameter-reduced portions 12 of various cross-sectional shapes as illustrated in (B)~(E) of FIG. 4. The diameter-reduced portion 12 is approximately crescent-shaped, triangular or rectangular in its cross-section and a width w and a height h wherein the ratio h/w is less than 0.5.

Figure 5:
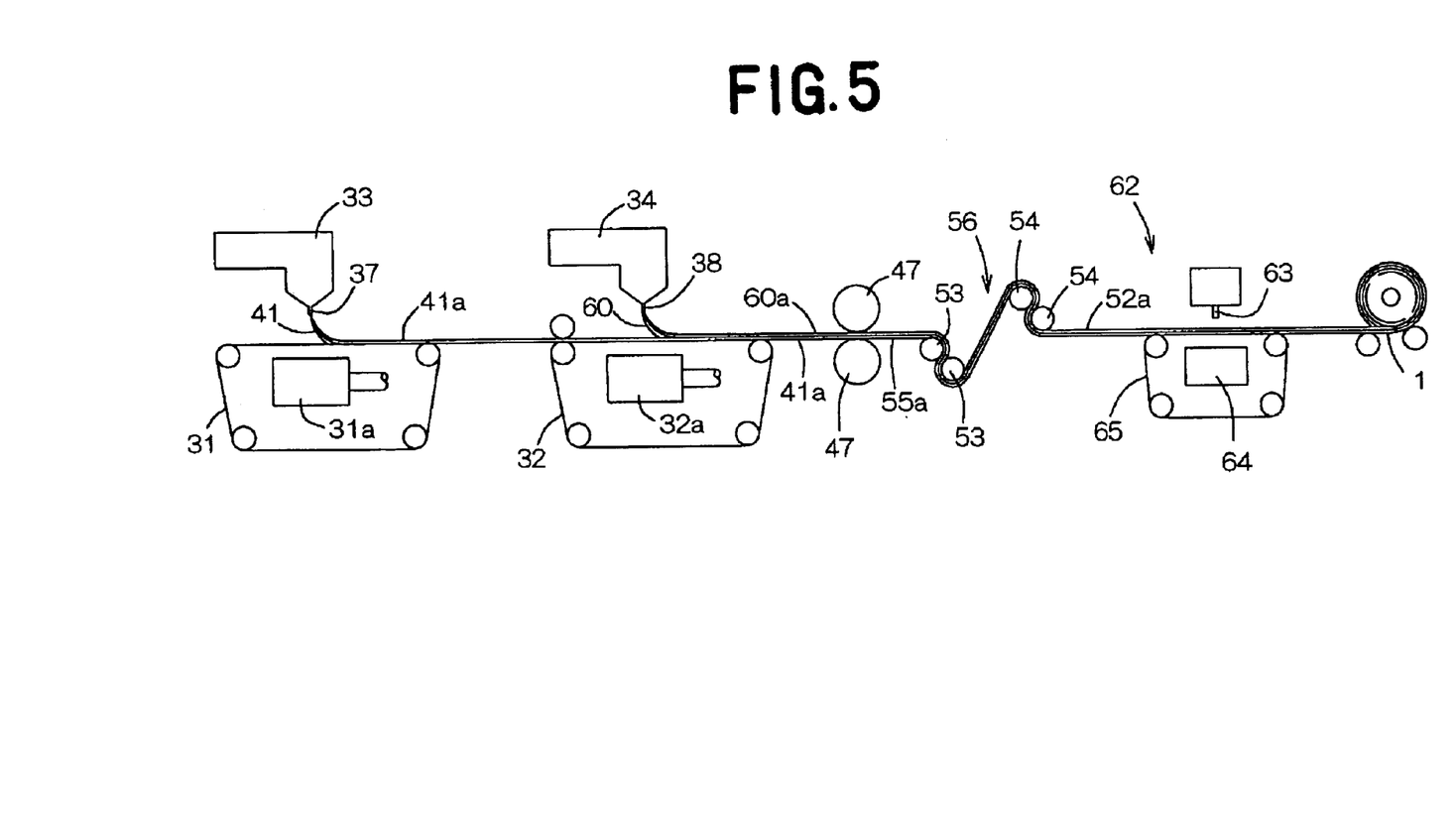
FIG. 5 is a schematic diagram illustrating a process for making the composite sheet.

FIG. 5 is a schematic diagram illustrating an example of the process for making the composite sheet. At the left in FIG. 5, first and second endless belts 31, 32 are successively provided, both adapted to run rightward. Above these endless belts 31, 32, first and second extruders 33, 34 are provided respectively. The extruders 33, 34 are respectively provided with arrays comprising a plurality of nozzles 37, 38, each of these arrays being arranged transversely of the endless belts 31, 32. Suction ducts 31a, 32a underlie the first and second extruders 33, 34, respectively, with the endless belts 31, 32 interposed there between.

The nozzles 37 associated with the first extruder 33 discharge a plurality of elastically stretchable first continuous fibers 41 of thermoplastic elastomer onto the first endless belt 31 under a suction effect of the duct 31a. The first continuous fibers 41 discharged in this manner are preferably welded together on the first endless belt 31 to form a stabilized first web 41a presenting a nonwoven fabric like form before transferred to the second endless belt 32. The nozzles 38 associated with the second extruder 34 discharge a plurality of inelastically stretchable continuous conjugated fibers 60 made of at least two types of thermoplastic synthetic resin onto the first web 41a under a suction effect of the duct 32a to form a conjugated fiber web 60a.

The first web 41a and the conjugated fiber web 60a placed upon each other are fed into a nip defined between a pair of heated calender rollers 47 on which the bonding zones 4

(See FIG. 1) are formed intermittently in the machine direction so that the first web 41a and the conjugated fiber web 60a are welded together at the bonding zones 4 to form composite web 55a. This composite web 55a is further transported in the machine direction to a stretching step 56 formed with a pair of front rollers 53 and a pair of rear rollers 54 in which the composite web 55a is stretched in the machine direction by a desired percentage, preferably by 40~300% and, at the same time, the conjugated fiber 60 is divided into the respective types of component resin preferably between each pair of the adjacent bonding zones 4, 4. The web 60a made of the conjugated fiber 60 is inelastically stretched in this stretching step 56 to form second web 52a. In this step 56, the rear roller 54 rotates at a peripheral speed higher than that of the front roller 53 so that the composite web 55a may be stretched in this step. The composite web 55a having left the rear roller 54 is transported, as it remains in stretched state or as it has been relieved of stretching effect and contracted substantially to its initial dimension, by a third endless belt 65 to a water stream treatment step 62. In this step 62, a plurality of nozzles 63 arranged transversely of the composite web 55a discharge high pressure columnar water streams against the second web 52a. The water streams are sucked by a duct 64 underlying the third endless belt 65. In this step 62, an amount of the conjugated fiber 60 which has not been divided is divided. The composite web 55a having left the step 62 passes through a contraction step (not shown) if it is still in stretched state, then through a drying step (not shown) and is taken up in a roll of the elastically stretchable composite sheet 1.

The first web 41a and the second web 52a as have been described above with respect to the process correspond to the lower layer 2 and the upper layer 3 shown in FIG. 1, respectively, and the conjugated fiber 60 as has been described above with respect to the process corresponds to the fiber 6 also shown in FIG. 1. The portions branched from the conjugated fiber 60 correspond to the diameter-reduced portions 12 of the fiber 6 (See FIG. 2) and the non-branched portions correspond to the diameter-enlarged portions 11 of the fiber 6.

In the stretching step 56 and the following contraction step for the composite web 55a of the process, the first web 41a is elastically stretched and then contract. The second web 52a obtains a permanent set generated due to inelastic stretch of the conjugated fiber 60 by an amount corresponding to that by which the conjugated fiber 60 has been stretched. This permanent set forms the diameter-reduced portions 12 and/or the diameter-enlarged portion 11 describing curves between each pair of the adjacent bonding zones 4, 4. The first web 41a is elastically stretched or contracted as the composite sheet 1 is stretched or contracted in the machine direction, i.e., in the y-direction in FIG. 1. The fiber 6 of the second web 52a is stretched in the y-direction to describe a straight line or contracted in the y-direction to describe a curve between each pair of the adjacent bonding zones 4, 4 as the first web 41a is elastically stretched or contracted.

The conjugated fiber 60 destined to become the fiber 6 comprises a combination of at least two types of poorly compatible resin. Such combination is not limited to the combination of polypropylene/polyester, but may be selected from a group of combinations such as polypropylene and polyethylene, polypropylene and nylon, polyester and nylon, polyester and polyethylene, and polyethylene and nylon. Such conjugated fiber 60 has its cross-section on the periphery of which interfaces of different types of resin appear and differential stretchability thereof causes the different types of resin to be peeled off one from another along the interfaces as the conjugated fiber 60 is stretched in the step 56. In this way, the branched or divided fibers are formed. The different type of resin constituting the conjugated fiber 60 are peeled off one from another along the interfaces to form the branched or divided fibers also when the conjugated fiber 60 is subjected to the high pressure columnar water streams. The branched or divided fibers obtained in this manner are destined to become the diameter-reduced portions 12 of the fiber shown in FIG. 2. If the conjugated fiber 60 is adequately branched or divided as the composite web 55a is stretched in the step 56, the subsequent water stream treatment step 62 will be unnecessary. It is also possible without departing from the scope of this invention to stretch the conjugated fiber 60 in the step 56 and to dividing the conjugated fiber 60 in the water stream treatment step 62. In this case, the conjugated fiber 60 which has a fineness less 20 dtex and can be divided in two or more can be used. A basis weight of the conjugated fiber 60 is preferably in a range of 2~100 g/m$^2$.

The process according to this invention is adapted to reduce the diameter of the conjugated fiber 60 in two steps by stretching the conjugated fiber 60 in the stretching step 56 and dividing this in the subsequent high pressure columnar water streams treatment step. Such step treatment enables the superfine diameter-reduced portion 12 having a fineness in the order of 0.05 dtex to be made. Cross-sectional shape of the diameter-reduced portion 12 can be controlled by configuration of the nozzle 38 used to spin the conjugated fiber 60. The composite sheet 1 and the process for making this according to this invention may exploited in an alternative manner in which the lower surface of the lower layer 2 also has a same inelastically stretchable fibrous layer as the upper layer 3 has, i.e., the first web 41a is provided on its upper and lower surfaces with the second webs 52a bonded thereto.

The elastically stretchable composite sheet according to one aspect of this invention is characterized in that the component fibers of the inelastically stretchable fibrous layer constituting this composite sheet are of a relatively low fineness and of a relatively flat cross-section defined by the ratio h/w less than 0.5 wherein w represents a height and h represents a width. Such unique arrangement facilitates the composite sheet to be easily deformed in its thickness direction and to offer a comfortably flexible touch. The component fibers in this fibrous layer include branched or divided conjugated fibers serving to reduce the fineness and facilitating sections of the fibers to be controlled in desired shapes. The process according to the other aspect of this invention is adapted to use the conjugated fiber having a relatively high fineness and being able to be discharged from the nozzle having a relatively large diameter. Compared to the case in which the conjugated fibers of the composite sheet are obtained by so-called melt blown process, the process according to this invention enables the amount of fibers produced by a sing nozzle per unit time to be remarkably increased.

What is claimed is:
1. An elastically stretchable composite sheet, comprising:
   a first web having x- and y-directions orthogonal to each other and being elastically stretchable at least in said y-direction; and
   a second web comprising thermoplastic synthetic resin fibers and being inelastically stretchable in said y-direction, said first and second webs being bonded to each other in bonding zones intermittently distributed in said y-direction;

wherein
- a length of each of said thermoplastic synthetic resin fibers that extends between each pair of the adjacent bonding zones where said thermoplastic synthetic resin fiber is bonded to said first web is longer than a straight distance between said adjacent bonding zones;
- said first web is a fibrous web comprising component fibers of elastic material;
- each of said thermoplastic synthetic resin fibers has a cross-section taken in a direction orthogonal to a longitudinal direction of said thermoplastic synthetic resin fiber, said cross section having a width w and a height h, as measured in orthogonal directions, dimensioned so that a ratio of h/w is less than 0.5;
- said second web further comprises sections of unsplit conjugate fibers, said thermoplastic synthetic resin fibers branching from the conjugate fibers which comprise at least two types of thermoplastic synthetic resin that are splittable into said thermoplastic synthetic resin fibers each made of one of said types of resin; and
- the sections of unsplit conjugate fibers are bonded to said first web in said bonding zones.

2. The composite sheet according to claim 1, wherein said cross section is a substantially rectangular cross-section having a long side that defines said width w and a short side that defines said height h.

3. The composite sheet according to claim 1, wherein said cross section is a substantially triangular cross-section having a base that defines said width w and a height that defines said height h.

4. A process of making an elastically stretchable composite sheet, said process comprising the steps of:
   a. continuously feeding a first web of elastic material in a direction;
   b. obtaining a plurality of conjugate fibers each comprising at least two types of thermoplastic synthetic resin that are separable from each other, and then continuously feeding said conjugate fibers in said direction as a second web;
   c. placing said first web and said second web of said conjugate fibers upon each other and bonding said first and second webs together in bonding zones arranged intermittently in said direction to form a composite web;
   d. after said bonding in step c, stretching said composite web in said direction with a sufficient stress to split said conjugate fibers up into split fibers of said types of thermoplastic synthetic resin, without splitting said conjugate fibers in said bonding zones where said conjugate fibers have been bonded to said first web; and
   e. allowing said stretched composite web to contract to obtain said composite sheet.

5. The process according to claim 4, further comprising a step of continuously feeding said composite web in stretched or contracted state and subjecting said conjugate fibers to high pressure columnar water streams discharged from a plurality of nozzles to split said conjugate fibers up into said split fibers.

6. The process according to claim 5, wherein each of the split fibers obtained in the step of stretching said composite web or in the step of subjecting said conjugate fibers to the high pressure columnar water streams has a cross-section taken in a direction orthogonal to a longitudinal direction of said split fiber, said cross-section being defined by a width w and a height h, and wherein a ratio of h/w is less than 0.5.

7. The process according to claim 4, wherein the step of obtaining said conjugate fibers comprises melt-spinning.

8. The process according to claim 4, further comprising the step of providing said first web which is a fibrous web comprising component fibers made of said elastic material.

9. The process according to claim 8, wherein the step of providing said first web includes
- discharging said component fibers from an extruder; and
- mechanically entangling or welding or adhesively bonding said component fibers with each other to form said first web.

10. The process according to claim 4, further comprising the step of providing said first web which is a non-woven fabric.

11. The process according to claim 4, further comprising the step of providing said first web which is a woven fabric.

12. The process according to claim 4, wherein said direction is a machine direction of said composite sheet.

13. The process according to claim 4, wherein said at least two types of thermoplastic synthetic resin have different stretchability degrees, allowing said conjugate fibers to split in said stretching step.

14. The process according to claim 4, consisting essentially of steps a) through e).

15. The composite sheet according to claim 1, wherein said first web is a non-woven fabric.

16. The composite sheet according to claim 1, wherein said first web is a woven fabric.

* * * * *

UNITED STATES PATENT AND TRADEMARK OFFICE
CERTIFICATE OF CORRECTION

PATENT NO. : 6,720,063 B2
DATED : April 13, 2004
INVENTOR(S) : Kobayashi et al.

It is certified that error appears in the above-identified patent and that said Letters Patent is hereby corrected as shown below:

<u>Title page,</u>
Item [73], Assignee, change "Kawanoe" to -- Kawanoe-Shi --
Item [30], Foreign Application Priority Data, change "Jan 9, 2000" to
-- Sept. 1, 2000 --

Signed and Sealed this

Twenty-fourth Day of May, 2005

JON W. DUDAS
*Director of the United States Patent and Trademark Office*